United States Patent [19]

Paul

[11] 4,268,525

[45] May 19, 1981

[54] AMIDOXIMETHER INSECTICIDES

[75] Inventor: Jill H. Paul, Edgewater, N.J.

[73] Assignee: Mobil Oil Corporation, New York, N.Y.

[21] Appl. No.: 144,758

[22] Filed: Apr. 28, 1980

[51] Int. Cl.³ .................... A01N 37/52; C07C 123/00
[52] U.S. Cl. .................... 424/326; 260/465 E; 560/35; 564/229
[58] Field of Search .......... 260/564 R, 564 G, 465 E; 424/326; 560/35

[56] References Cited

U.S. PATENT DOCUMENTS

| 3,394,181 | 7/1968 | Bell | 260/564 G |
| 4,152,454 | 5/1979 | Plapp, Jr. | 424/326 |
| 4,183,957 | 1/1980 | Pawloski | 260/564 R |

Primary Examiner—Natalie Trousof
Assistant Examiner—L. Hendriksen
Attorney, Agent, or Firm—Charles A. Huggett; Hastings S. Trigg

[57] ABSTRACT

This invention is concerned with certain aryl amidoxime ethers of 3-phenoxybenzyl alcohol, which have insecticidal activity.

18 Claims, No Drawings

AMIDOXIMETHER INSECTICIDES

BACKGROUND OF THE INVENTION

1. Field of the Invention

This invention is concerned with certain aryl amidoxime ethers of 3-phenoxybenzyl alcohol, which have insecticidal activity.

2. Description of the Prior Art

In Japanese Pat. No. 154,426, there are disclosed pyrethroid alcohol esters of substituted phenyl-α-dimethylaminoacetic acid having insecticidal activity. Insofar as is now known, the amidoxime ethers of this invention have not been proposed.

SUMMARY OF THE INVENTION

This invention provides compounds having the formula:

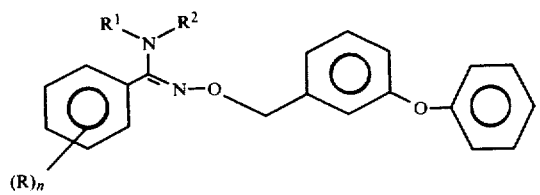

wherein R is halogen, $C_1-C_6$ alkyl, $C_1-C_6$ alkoxy, $C_2-C_6$ alkenyl, $C_1-C_6$ alkylthio, $C_1-C_6$ haloalkyl, trifluoromethyl, trifluoromethoxy, difluoromethoxy, trifluoromethylthio, difluoromethylthio, $C_1-C_6$ alkylamino, cyano; nitro, $C_1-C_6$ carboalkoxy, $C_1-C_6$ alkylsulphonyl, $C_1-C_6$ alkoxy $C_1-C_6$ alkyl, $C_2-C_6$ haloalkenyl, or $C_1-C_6$ acyl; n is 0-5; $R^1$ and $R^2$ are hydrogen, $C_1-C_6$ alkyl, $C_3-C_6$ cycloalkyl, $C_1-C_6$ alkylcycloalkyl ($C_3-C_6$), or $C_2-C_6$ alkenyl.

DESCRIPTION OF SPECIFIC EMBODIMENTS

Non-limiting examples of the compounds of this invention are:

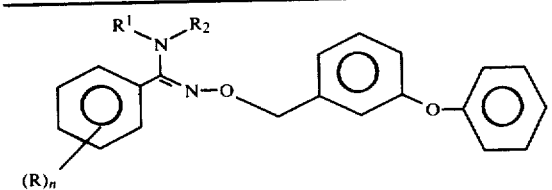

| R | $R^1$ | $R^2$ |
|---|---|---|
| — | H | $CH_3$ |
| 4-$C_2H_5$ | H | cyclopropyl |
| 2,4-difluoro | $CH_3$ | $CH_3$ |
| 3-$CH_3O$ | $C_2H_5$ | $C_2H_5$ |
| 4-Br | H | $C_4H_9$ |
| 4-allyl | $CH_3$ | $CH_3$ |
| 3-$C_2H_5S$ | H | allyl |
| 4-$CClF_2$ | H | hexenyl |
| 4-$CF_3O$ | H | $C_2H_5$ |
| 4-$CF_3S$ | H | H |
| 4-$CF_2HO$ | $CH_3$ | $CH_3$ |
| 4-$CF_2HS$ | H | cyclobutyl |
| 4-$C_3H_7NH$ | H | methylcyclohexyl |
| 3-$NO_2$ | $CH_3$ | $C_2H_5$ |
| 4-CN | H | $C_6H_{13}$ |
| 4-$COOC_2H_5$ | H | $C_4H_9$ |
| 4-$CH_3SO_2$ | $CH_3$ | $CH_3$ |
| 4-$CH_3COO$ | H | $C_3H_7$ |

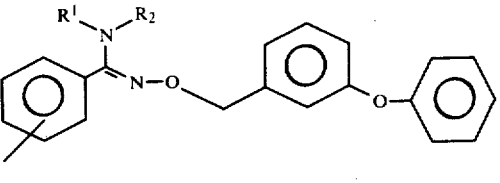

| R | $R^1$ | $R^2$ |
|---|---|---|
| 4-CHCl=C(H)— | H | $CH_3$ |

The compounds of this invention are prepared in accordance with the following series of steps:

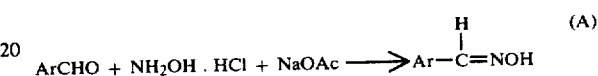 (A)

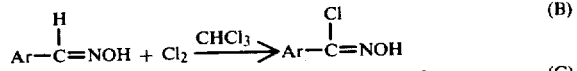 (B)

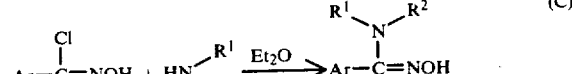 (C)

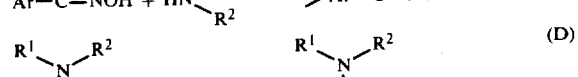 (D)

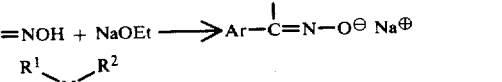

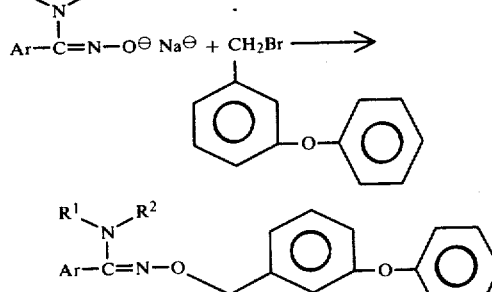

The ArCHO reactants in step (A), i.e., benzaldehyde and substituted benzaldehydes, are obtained from commercial sources.

GENERAL PROCEDURE A FOR BENZALDOXIMES

In general, the benzaldehydes were dissolved in methanol and refluxed 3-5 hours in the presence of an excess of hydroxylamine hydrochloride and sodium acetate in $H_2O$. The reaction mixture was quenched with $H_2O$ and the oxime was extracted into an organic solvent. Recrystallization from either hexane, hexane/$CHCl_3$ or $EtOH/H_2O$ followed.

GENERAL PROCEDURE B FOR ARYL HYDROXAMOYL CHLORIDES

A solution of p-chlorobenzaldoxime (1.0 g., 0.0065 mole) in 20 ml. chloroform was cooled to −50° C. Gaseous chlorine was bubbled through the solution at such a rate as to maintain the temperature below 0° C. (−10° to 0° C.). Chlorine addition was stopped after the solution changed from colorless to blue to green. Minor amounts of solids were filtered and washed with chloroform. The filtrate was evaporated under reduced pressure to yield 0.7 g. (0.0037 mole) of product as an off-white solid (m.p. 86°-87° C.).

GENERAL PROCEDURE C FOR ARYL AMIDOXIMES p-Chlorophenyl hydroxamoyl chloride (0.7 g., 0.0037 mole) was dissolved in 20 ml. of diethyl ether. One milliliter (0.011 mole) of isopropylamine in 10 ml. of diethyl ether was added dropwise, immediately causing precipitation of isopropylamine hydrochloride. The reaction mixture was stirred at room temperature for 2 hours, followed by quenching with 50 ml. H2O. The layers were separated and the aqueous layer was extracted once with diethyl ether. The combined organic extracts were washed twice with water, dried, and evaporated to yield 0.6 g. (0.0028 mole) of product.

GENERAL PROCEDURE D FOR AMIDOXIMETHERS

A solution of 0.02 mole of amidoxime in 20 ml. of ethanol is added to a freshly prepared ethanolic solution of 0.02 mole NaOEt. The mixture is stirred at room temperature for 30 minutes and concentrated under reduced pressure to dryness. The resulting sodium oximate salt is dissolved in a minimum volume of 90% DMF and 10% t-butanol, whereupon 0.02 mole of 3-phenoxybenzyl bromide is added dropwise, causing an exotherm of ~8°. The reaction mixture is stirred overnight at room temperature and poured into H2O. The resulting oil is extracted two times into toluene. The combined organic layers are washed with 5% NaOH (50:50 H2O/ethanol), H2O, dried over MgSO4 and concentrated under reduced pressure to yield 0.15-0.19 mole of >90% pure product.

Using the aforedescribed general procedures, the following compounds were prepared.

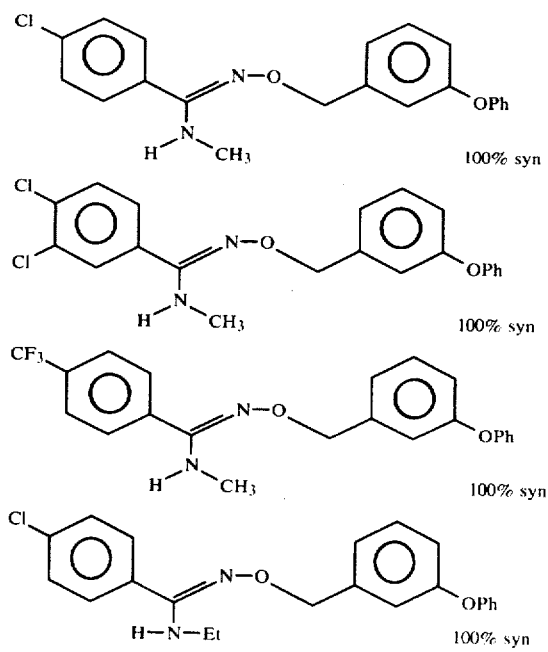

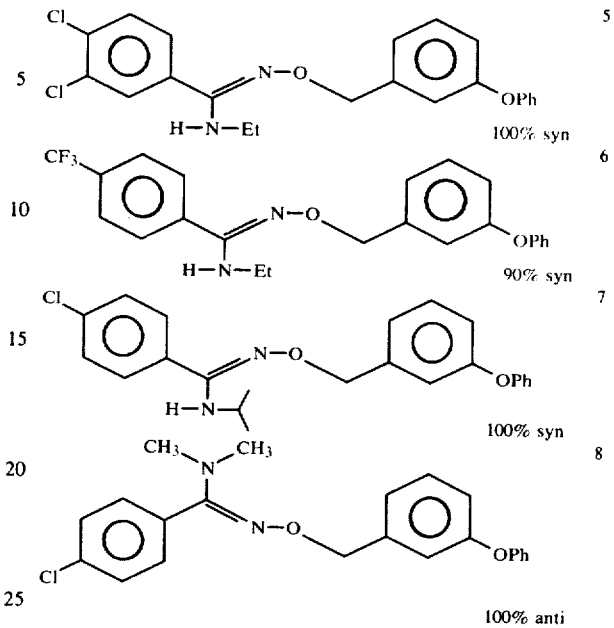

The compounds of this invention have been found to exhibit considerable biological activity. They are especially potent pesticides when used to control or combat important agricultural pests. These compounds can be used in various ways to achieve biological action. They can be applied per se, as solids or in vaporized form, but are preferably applied as the toxic components in pesticidal compositions of the compound and a carrier. The compositions can be applied as dusts, as liquid sprays, or as gas-propelled sprays and can contain, in addition to a carrier, additives such as emulsifying agents, wetting agents, binding agents, gases compressed to the liquid state, odorants, stabilizers and the like. A wide variety of liquid and solid carriers can be used in the pesticidal compositions. Non-limiting examples of liquid carriers include water; organic solvents such as alcohols, ketones, amides, and esters; mineral oils such as kerosene, light oils, and medium oils, and vegetable oils such as cottonseed oil. Non-limiting examples of solid carriers include talc, bentonite, diatomaceous earth, pyrophyllite, fullers earth, gypsum, flours derived from cottonseeds and nut shells, and various natural and synthetic clays having a pH not exceeding about 9.5.

The amount of the compounds of this invention utilized in pesticidal compositions will vary rather widely. It depends to some extent upon the type of composition in which the material is being used, the nature of the condition to be controlled, and the method of application (e.i., spraying, dusting, etc.). In the ultimate pesticidal composition, as applied in the field, pesticide concentrations as low as 0.0001 weight percent of the total composition can be used. In general, compositions, as applied, containing about 0.05 weight percent pesticide in either liquid or solid carrier, give excellent results. In some cases, however, stronger dosages up to about 10 weight percent may be required.

In practice, pesticidal compositions are usually prepared in the form of concentrates, which are diluted in the field to the concentration desired for application. For example, the concentrate can be a wettable powder containing large amounts of the compound of this invention, a carrier (e.g., attapulgite or other clay), and wetting and dispersing agents. Such powders can be diluted prior to application, by dispersing it in water to obtain a sprayable suspension containing the concentration of pesticide desired for application. Other concentrates can be solutions that can be later diluted, e.g., with kerosene. Thus, it is within the contemplation of this invention to provide pesticidal compositions containing up to about 80%, by weight of the composition, of a pesticidal compound of this invention. Accordingly, depending upon whether it is ready for application or it is in concentrated form, the contemplated pesticidal compositions contain between about 0.0001 percent and about 80 percent, by weight of the compositions, of a pesticidal compound of this invention and a carrier, liquid or solid, as defined hereinbefore.

INSECTICIDE TEST METHODS

Bait Test [Housefly (Adult)]

Method of Treatment

One milliliter of an aqueous solution or suspension of the candidate compound is pipetted into a 9 cm. petri dish containing filter paper and 0.1 gm. granular sugar. Ten adults are admitted and the dish is closed.

Method of Recording Results

Mortality is recorded after 24-75 hours. Compounds which produce 90% mortality are reevaluated at lower concentrations in secondary tests. Mode of action may be by stomach poison, contact or vapor.

Stomach Poison—Foliar Dip Test

Primary Screen
Southern Armyworm (Larva)
Mexican Bean Beetle (Larva)

Method of Treatment

Lima bean leaves of a uniform size are momentarily dipped in a 500 ppm. water-acetone of the test material. Treated leaves are placed on moistened filter paper in 9 cm. petri dishes and allowed to air dry, and then are infested. The dishes are then closed.

Method of Recording Results

Mortality is recorded 72 hours after infestation. Compounds active at 500 ppm. are retested at 100 and 10 ppm.

All test results are recorded as percent mortality. In the tabulation of data, the insect species are abbreviated as follows: Housefly (HF), Mexican Bean Beetle (MB), and Southern Armyworm (SA).

Examples 1-8 were subjected to the aforedescribed insecticide tests. Test concentrations and results are set forth in the Table.

TABLE

| Compound | Rate (PPM) | HF | SA | MB |
| --- | --- | --- | --- | --- |
| Example 1 | 500 | 40 | 90 | 100 |
|  | 100 |  | 90 | 85 |
|  | 40 |  | 25 | 0 |
| Example 2 | 500 | 70 | 60 | 100 |
|  | 100 |  |  | 100 |
| Example 3 | 500 | 100 | 100 | 100 |
|  | 100 | 90 | 50 | 95 |
|  | 10 |  | 0 | 65 |
| Example 4 | 500 | 100 | 100 | 100 |
|  | 100 | 85 | 40 | 85 |
|  | 10 |  | 0 | 25 |
| Example 5 | 500 | 100 | 100 | 100 |
|  | 100 | 60 | 10 | 95 |
|  | 10 | 20 | 0 | 15 |
| Example 6 | 500 | 100 | 100 | 100 |
|  | 100 | 100 | 90 | 85 |

TABLE-continued

| Compound | Rate (PPM) | HF | SA | MB |
| --- | --- | --- | --- | --- |
|  | 10 | 50 | 5 | 55 |
| Example 7 | 500 | 100 | 100 | 95 |
|  | 100 | 55 | 25 | 85 |
|  | 10 | — | 0 | 0 |
| Example 8 | 500 | 20 | 70 | 100 |
|  | 100 |  |  | 80 |

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. Insecticidal compounds having the formula:

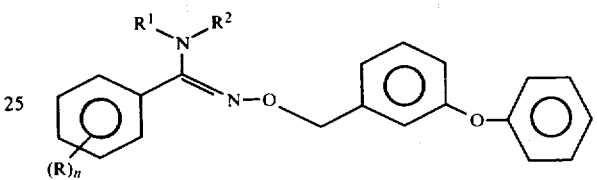

wherein R is halogen, $C_1-C_6$ alkyl, $C_1-C_6$ alkoxy, $C_2-C_6$ alkenyl, $C_1-C_6$ alkylthio, $C_1-C_6$ haloalkyl, trifluoromethyl, trifluoromethoxy, difluoromethoxy, trifluoromethylthio, difluoromethylthio, $C_1-C_6$ alkylamino, cyano; nitro, $C_1-C_6$ carboalkoxy, $C_1-C_6$ alkylsulphonyl, $C_1-C_6$ alkoxy $C_1-C_6$ alkyl, $C_2-C_6$ haloalkenyl, or $C_1-C_6$ acyl; n is 0-5, $R^1$ and $R^2$ are hydrogen, $C_1-C_6$ alkyl, $C_3-C_6$ cycloalkyl, $C_1-C_6$ alkylcycloalkyl $(C_3-C_6)$, or $C_2-C_6$ alkenyl.

2. A compound of claim 1 having the formula:

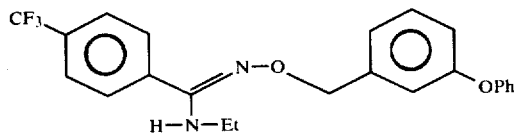

3. A compound of claim 1 having the formula:

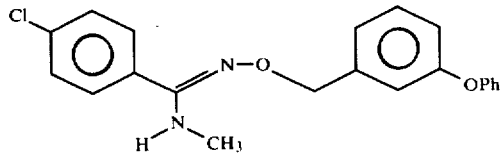

4. A compound of claim 1 having the formula:

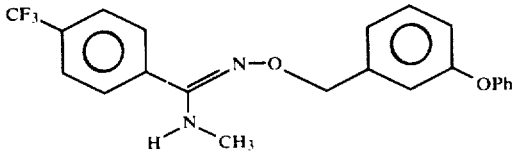

5. A compound of claim 1 having the formula:

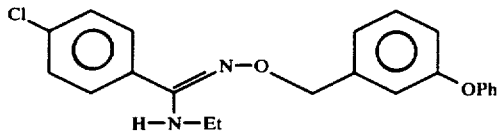

6. A compound of claim 1 having the formula:

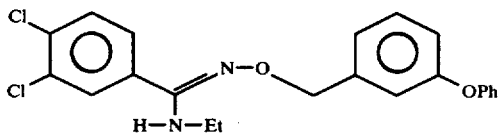

7. An insecticidal composition comprising a carrier and an insecticidal amount of a compound of claim 1.

8. An insecticidal composition comprising a carrier and an insecticidal amount of a compound of claim 2.

9. An insecticidal composition comprising a carrier and an insecticidal amount of a compound of claim 3.

10. An insecticidal composition comprising a carrier and an insecticidal amount of a compound of claim 4.

11. An insecticidal composition comprising a carrier and an insecticidal amount of a compound of claim 5.

12. An insecticidal composition comprising a carrier and an insecticidal amount of a compound of claim 6.

13. The method of combatting insects that comprises contacting them with an insecticidal amount of a compound of claim 1.

14. The method of combatting insects that comprises contacting them with an insecticidal amount of a compound of claim 2.

15. The method of combatting insects that comprises contacting them with an insecticidal amount of a compound of claim 3.

16. The method of combatting insects that comprises contacting them with an insecticidal amount of a compound of claim 4.

17. The method of combatting insects that comprises contacting them with an insecticidal amount of a compound of claim 5.

18. The method of combatting insects that comprises contacting them with an insecticidal amount of a compound of claim 6.

* * * * *